(12) United States Patent
Kennedy et al.

(10) Patent No.: US 8,552,118 B2
(45) Date of Patent: Oct. 8, 2013

(54) POLYISOBUTYLENES AND PROCESS FOR MAKING SAME

(75) Inventors: Joseph P. Kennedy, Akron, OH (US); Yongmoon Kwon, Copley, OH (US); Subramanyam Ummadisetty, Hattiesburg, MS (US)

(73) Assignee: The University of Akron, Akron, OH (US)

( * ) Notice: Subject to any disclaimer, the term of this patent is extended or adjusted under 35 U.S.C. 154(b) by 810 days.

(21) Appl. No.: 12/516,270

(22) PCT Filed: Nov. 30, 2007

(86) PCT No.: PCT/US2007/024674
§ 371 (c)(1),
(2), (4) Date: Jan. 20, 2010

(87) PCT Pub. No.: WO2008/066914
PCT Pub. Date: Jun. 5, 2008

(65) Prior Publication Data
US 2010/0130696 A1    May 27, 2010

Related U.S. Application Data

(60) Provisional application No. 60/861,802, filed on Nov. 30, 2006, provisional application No. 60/959,065, filed on Jul. 11, 2007.

(51) Int. Cl.
*C08F 4/00* (2006.01)
*C08F 132/00* (2006.01)

(52) U.S. Cl.
USPC .................................. 525/244; 525/332.3

(58) Field of Classification Search
USPC .............. 525/379, 384, 386, 263, 244, 332.3; 526/348.7
See application file for complete search history.

(56) References Cited

U.S. PATENT DOCUMENTS

| | | |
|---|---|---|
| 2,819,319 A | 1/1958 | Barnes |
| 4,960,938 A | 10/1990 | O'Reilly |
| 5,414,095 A | 5/1995 | Harris |
| 2006/0106173 A1 * | 5/2006 | Karl et al. ............. 525/263 |
| 2006/0142503 A1 | 6/2006 | Lang |

FOREIGN PATENT DOCUMENTS

| | | | |
|---|---|---|---|
| CA | 2005295960 | * | 4/2012 |
| WO | WO 98/02468 A1 | | 1/1998 |
| WO | WO 0132730 A1 | | 5/2001 |

OTHER PUBLICATIONS

Li, et al: "Polyisobutylene supports-anon-polar hydrocarbon analog of PEG supports", Tetrahedron, Elsevier Science Pub, Amsterdam, NL, vol. 61, No. 51, 2005, 12081-12084.
Chang, V.S.C., et al. "End Group Determination in Hydroxyl-Telechelic Polyisobutylenes by Infrared Spectroscopy", Polymer Bul., Vo. 9, 1983, 518-524.
Binder, et al., "Novel Synthetic Routes to Aminfunctionalized Polyisobutylenes", Polymer Preprints, 2003 44(2), p. 85.
Wilczek, Lech and Kennedy, Joseph P., "Electrophilic Substitution of Organosilicon Compounds. II. Synthesis of Allyl-Terminated Polyisobutylenes by Quantitative Allylation of tert-Chloro-Polyisobutylenes with Allyltrimethylsilane", The Journal of Polymer Science: Part A: Polymer Chemistry, vol. 25, pp. 3255-3265 (1987).

* cited by examiner

*Primary Examiner* — Ling Choi
*Assistant Examiner* — Monique Peets
(74) *Attorney, Agent, or Firm* — Renner Kenner Greive Bobak Taylor & Weber

(57) ABSTRACT

The present invention generally relates to alcohol-terminated polyisobutylene (PIB) compounds, and to a process for making such compounds. In one embodiment, the present invention relates to primary alcohol-terminated polyisobutylene compounds, and to a process for making such compounds. In still another embodiment, the present invention relates to polyisobutylene compounds that can be used to synthesize polyurethanes, to polyurethane compounds made via the use of such polyisobutylene compounds, and to processes for making such compounds. In yet another embodiment, the present invention relates to primary alcohol-terminated polyisobutylene compounds having two or more primary alcohol termini and to a process for making such compounds. In yet another embodiment, the present invention relates to primary terminated polyisobutylene compounds having two or more primary termini selected from amine groups or methacrylate groups.

7 Claims, 3 Drawing Sheets

A)

B)

POLYISOBUTYLENES AND PROCESS FOR MAKING SAME

The present invention was made in the course of research that was supported by National Science Foundation (NSF) Grant DMR 02-43314-3. The United States government may have certain rights to the invention or inventions herein.

FIELD OF THE INVENTION

The present invention generally relates to alcohol-terminated polyisobutylene (PIB) compounds, and to a process for making such compounds. In one embodiment, the present invention relates to primary alcohol-terminated polyisobutylene compounds, and to a process for making such compounds. In still another embodiment, the present invention relates to polyisobutylene compounds that can be used to synthesize polyurethanes, to polyurethane compounds made via the use of such polyisobutylene compounds, and to processes for making such compounds. In yet another embodiment, the present invention relates to primary alcohol-terminated polyisobutylene compounds having two or more primary alcohol termini and to a process for making such compounds. In yet another embodiment, the present invention relates to primary terminated polyisobutylene compounds having two or more primary termini selected from amine groups or methacrylate groups.

BACKGROUND OF THE INVENTION

Various polyurethanes (PUs) are multibillion dollar commodities and are manufactured worldwide by some of the largest chemical companies (e.g., Dow, DuPont, BASF, and Mitsui). Polyurethanes are used in a wide variety of industrial and clinical applications in the form of, for example, thermoplastics, rubbers, foams, upholstery, tubing, and various biomaterials.

Typically, PUs are made by combining three ingredients: (1) a diol (such as tetramethylene oxide); (2) a diisocyanate (such as 4,4'-methylene diphenyl diisocyanate); and (3) an extender (such as 1,4-butane dial). Generally, polyurethanes (Pus) contain a soft (rubbery) and a hard (crystalline) component; and the properties of PUs depend on the nature and relative concentration of the soft/hard components.

Even though primary alcohol-terminated PIB compounds, such as $HOCH_2$—PIB—$CH_2OH$, have been prepared in the past previous synthesis methods have been uneconomical. As such, the cost of manufacturing primary alcohol-terminated PIB compounds has been too high for commercial production. One reason for the high cost associated with manufacturing primary alcohol-terminated PIB compounds, such as $HOCH_2$—PIB—$CH_2OH$, is that the introduction of a terminal $CH_2OH$ group at the end of the PIB molecule necessitates the use of the hydroboration/oxidation method—a method that requires the use of expensive boron chemicals ($H_6B_2$ and its complexes). Given the above, numerous efforts have been made to develop an economical process for manufacturing primary alcohol-terminated PIB compounds, such as $HOCH_2$—PIB—$CH_2OH$. For example, BASF has spent millions of dollars on the research and development of a process to make $HOCH_2$—PIB—$CH_2OH$ by hydroboration/oxidation, where such a process permitted the recovery and reuse of the expensive boron containing compounds used therein. Other research efforts have been made, and have met with limited success in reducing the cost associated with producing primary alcohol-terminated PIB compounds, such as PIB—$CH_2OH$ or $HOCH_2$—PIB—$CH_2OH$.

With regard to amine-terminated PIBs, early efforts directed toward the synthesis of amine-terminated telechelic PIBs were both cumbersome and expensive, and the final structures of the amine-telechelic PIBs are different from those described below.

More recently, Binder et al. (see, e.g., D. Machl, M. J. Kunz and W. H. Binder, *Polymer Preprints*, 2003, 44(2), p. 85) initiated the living polymerization of isobutylene under well-known conditions, terminated the polymer with 1-(3-bromopropyl)-4-(1-phenylvinyl)-benzene, and effected a complicated series of reactions on the product to obtain amine-terminated PIBs. Complex structures very different from those disclosed herein were obtained and the above method did not yield amine-terminated telechelic PIB compounds that carry 1.0±0.05 functional groups.

Given the above, there is a need in the art for a manufacturing process that permits the efficient and cost-effective production/manufacture of primary alcohol-terminated PIB compounds, primary amine-terminated PIB compounds, primary methacrylate-terminated PIB compounds, and/or primary amine-terminated telechelic PIB compounds.

SUMMARY OF THE INVENTION

The present invention generally relates to alcohol-terminated polyisobutylene (PIB) compounds, and to a process for making such compounds. In one embodiment, the present invention relates to primary alcohol-terminated polyisobutylene compounds, and to a process for making such compounds. In still another embodiment, the present invention relates to polyisobutylene compounds that can be used to synthesize polyurethanes, to polyurethane compounds made via the use of such polyisobutylene compounds, and to processes for making such compounds. In yet another embodiment, the present invention relates to primary alcohol-terminated polyisobutylene compounds having two or more primary alcohol termini and to a process for making such compounds. In yet another embodiment, the present invention relates to primary terminated, polyisobutylene compounds having two or more primary termini selected from amine groups or methacrylate groups.

In one embodiment, the present invention relates to a method for producing a primary alcohol-terminated polyisobutylene compound comprising the steps of: (A) providing an alkenyl-terminated polyisobutylene having at least two alkenyl termini, wherein the alkenyl termini are formed from straight or branched $C_3$ to $C_{12}$ alkenyl groups having a double bond present at the end of the alkenyl group; (B) subjecting the alkenyl-terminated polyisobutylene to anti-Markovnikov bromination to form a primary bromine-terminated polyisobutylene compound having at least two primary bromine termini; (C) converting the primary bromine-terminated polyisobutylene compound to a primary alcohol-terminated polyisobutylene via a base reaction, the primary alcohol-terminated polyisobutylene having at least two primary alcohol termini; and (D) recovering the primary alcohol-terminated polyisobutylene.

In another embodiment, the present invention relates to a primary alcohol-terminated polyisobutylene compound according to the following formula:

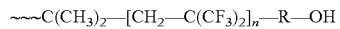

where ~~~ represents the remaining portion of a linear, star, hyperbranched, or arborescent molecule, n is an integer from 2 to about 5,000, and R is a straight or branched $C_3$ to $C_{12}$ linkage formed from a corresponding straight or branched $C_3$ to $C_{12}$ alkenyl group having a double bond present at the end of the alkenyl group, and where the primary alcohol-terminated polyisobutylene has at least two primary alcohol termini.

In still another embodiment, the present invention relates to a method for producing a primary methacrylate-terminated polyisobutylene compound comprising the steps of: (a) providing an alkenyl-terminated polyisobutylene having at least two alkenyl termini, wherein the alkenyl termini are formed from straight or branched $C_3$ to $C_{12}$ alkenyl groups having a double bond present at the end of the alkenyl group; (b) subjecting the alkenyl-terminated polyisobutylene to anti-Markovnikov bromination to form a primary bromine-terminated polyisobutylene compound having at least two primary bromine termini; (c) converting the primary bromine-terminated polyisobutylene compound to a primary methacrylate-terminated polyisobutylene via a reaction with at least one alkaline methacrylate compound, the primary methacrylate-terminated polyisobutylene having at least two primary methacrylate termini; and (d) recovering the primary methacrylate-terminated polyisobutylene.

In still yet another embodiment, the present invention relates to a primary methacrylate-terminated polyisobutylene compound according to the following formula:

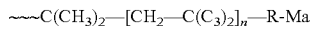

where ~~~ represents the remaining portion of a linear, star, hyperbranched, or arborescent molecule, n is an integer from 2 to about 5,000, R is a straight or branched $C_3$ to $C_{12}$ linkage formed from a corresponding straight or branched $C_3$ to $C_{12}$ alkenyl group having a double bond present at the end of the alkenyl group, and Ma represents a methacrylate termini, and where the primary methacrylate-terminated polyisobutylene has at least two primary methacrylate termini.

In still yet another embodiment, the present invention relates to a method for producing a primary amine-terminated polyisobutylene compound comprising the steps of: (i) providing an alkenyl-terminated polyisobutylene having at least two alkenyl termini, wherein the alkenyl termini are formed from straight or branched $C_3$ to $C_{12}$ alkenyl groups having a double bond present at the end of the alkenyl group; (ii) subjecting the alkenyl-terminated polyisobutylene to anti-Markovnikov bromination to form a primary bromine-terminated polyisobutylene compound having at least two primary bromine termini; (iii) converting the primary bromine-terminated polyisobutylene compound to a primary phthalimide-terminated polyisobutylene via a reaction with at least one alkaline phthalimide compound, the primary phthalimide-terminated polyisobutylene having at least two primary phthalimide termini; (iv) converting the primary phthalimide-terminated polyisobutylene compound to a primary amine-terminated compound via a reaction with an amine hydrate compound; and (v) recovering the primary amine-terminated polyisobutylene.

In still yet another embodiment, the present invention relates to a primary amine-terminated polyisobutylene compound according to the following formula:

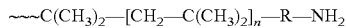

where ~~~ represents the remaining portion of a linear, star, hyperbranched, or arborescent molecule, n is an integer from 2 to about 5,000, and R is a straight or branched $C_3$ to $C_{12}$ linkage formed from a corresponding straight or branched $C_3$ to $C_{12}$ alkenyl group having a double bond present at the end of the alkenyl group, and where the primary amine-terminated polyisobutylene has at least two primary meth acrylate termini.

In still yet another embodiment, the present invention relates to a method for producing a primary bromine-terminated polyisobutylene compound comprising the steps of: providing an alkenyl-terminated polyisobutylene having at least two alkenyl termini, wherein the alkenyl termini are formed from straight or branched $C_3$ to $C_{12}$ alkenyl groups having a double bond present at the end of the alkenyl group; subjecting the alkenyl-terminated polyisobutylene to anti-Markovnikov bromination to form a primary bromine-terminated polyisobutylene compound having at least two primary bromine termini; and recovering the primary bromine-terminated polyisobutylene.

In still yet another embodiment, the present invention relates to a primary bromine-terminated polyisobutylene compound according to the following formula:

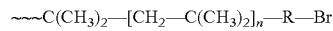

where ~~~ represents the remaining portion of a linear, star, hyperbranched, or arborescent molecule, n is an integer from 2 to about 5,000, and R is a straight or branched $C_3$ to $C_{12}$ linkage formed from a corresponding straight or branched $C_3$ to $C_{12}$ alkenyl group having a double bond present at the end of the alkenyl group, and where the primary bromine-terminated polyisobutylene has at least two primary bromine termini.

DETAILED DESCRIPTION OF THE INVENTION

Figure 1:
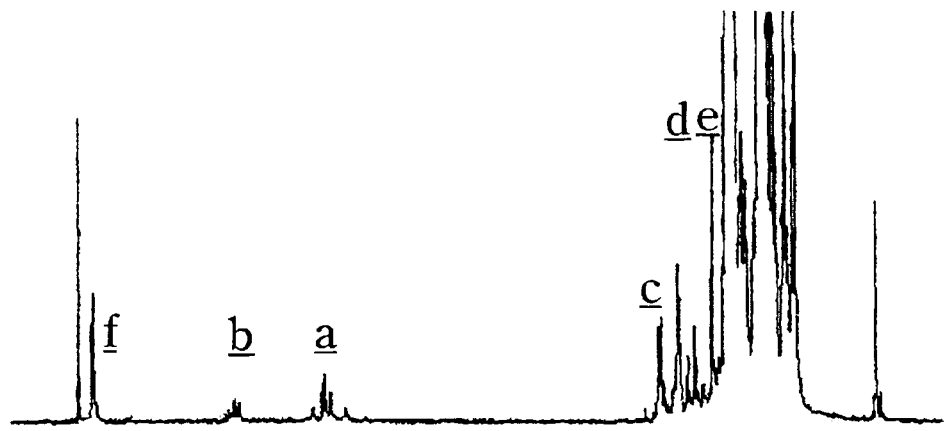
FIG. 1A is a $^1$H NMR spectrum of a three-arm star PIB molecule where the arm segments are-terminated with allyl groups (ø-(PIB-Allyl)$_3$)
FIG. 1B is a $^1$H NMR spectrum of a three-arm star PIB molecule where the arm segments are-terminated with primary bromines (—CH$_2$—Br)
Figure 1:
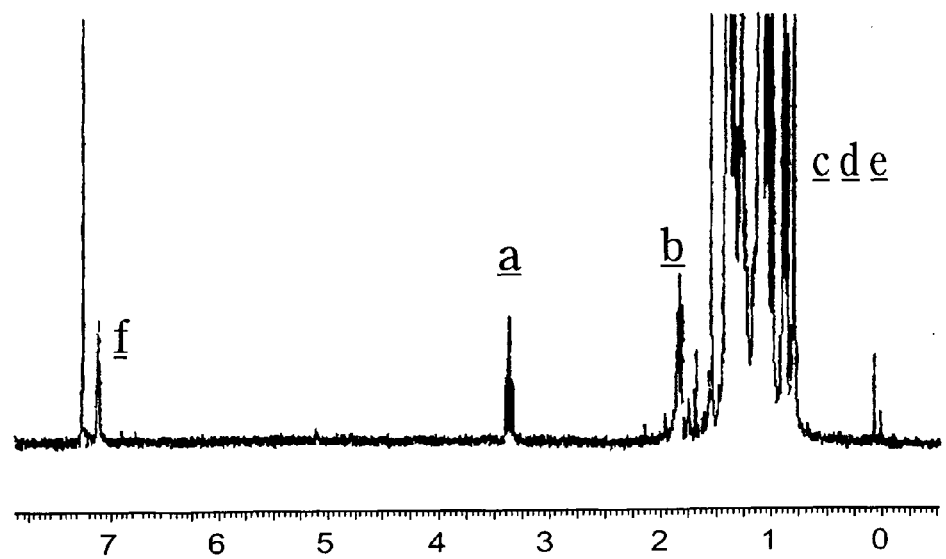

The present invention generally relates to alcohol-terminated polyisobutylene (PIB) compounds, and to a process for making such compounds. In one embodiment, the present invention relates to primary alcohol-terminated polyisobutylene compounds, and to a process for making such compounds. In still another embodiment, the present invention relates to polyisobutylene compounds that can be used to synthesize polyurethanes, to polyurethane compounds made via the use of such polyisobutylene compounds, and to processes for making such compounds. In yet another embodiment, the present invention relates to primary alcohol-terminated polyisobutylene compounds having two or more primary alcohol termini and to a process for making such compounds. In yet another embodiment, the present invention relates to primary terminated polyisobutylene compounds having two or more primary termini selected from amine groups or methacrylate groups.

Although the present invention specifically discloses a method for producing various PIB molecules-terminated with one —CH$_2$—CH$_2$—CH$_2$—OH group, the present invention is not limited thereto. Rather, the present invention can be used to produce a wide variety of PIB molecular geometries, where such molecules are-terminated with one or more primary alcohols.

In one embodiment, the primary alcohols that can be used as terminating groups in the present invention include, but are not limited to, any straight or branched chain primary alcohol substituent group having from 1 to about 12 carbon atoms, or from 1 to about 10 carbon atoms, or from 1 to about 8, or from about 1 to about 6 carbon atoms, or even from about 2 to about 5 carbon atoms. Here, as well as elsewhere in the specification and claims, individual range limits can be combined to form alternative non-disclosed range limits.

In one embodiment, the present invention relates to linear, or star-shaped, or hyperbranched, or arborescent PIB compounds, where such compounds contain one or more primary alcohol-terminated segments. Such molecular geometries are known in the art, and a discussion herein is omitted for the sake of brevity. In another embodiment, the present invention relates to star-shaped molecules that contain a center cyclic group (e.g., an aromatic group) to which three or more primary alcohol-terminated PIB arms are attached.

The following examples are exemplary in nature and the present invention is not limited thereto. Rather, as is noted above, the present invention relates to the production and/or manufacture of various PIB compounds and polyurethane compounds made therefrom.

EXAMPLES

The following example concerns the synthesis of a primary hydroxyl-terminated polyisobutylene in three steps:

1. Preparation of a Star Molecule with Three Allyl-Terminated PIB Arms (ø-(PIB-Allyl)$_3$):

The synthesis of ø-(PIB-Allyl)$_3$ followed the procedure described by Lech Wilczek and Joseph P. Kennedy in *The Journal of Polymer Science: Part A: Polymer Chemistry*, 25, pp. 3255 through 3265 (1987), the disclosure of which is incorporated by reference herein in its entirety.

The first step involves the polymerization of isobutylene to tert-chlorine-terminated PIB by the 1,3,5-tri(2-methoxyisopropyl)benzene/TiCl$_4$ system under a blanket of N$_2$ in a drybox. Next, in a 500 mL three-neck round bottom glass flask, equipped with an overhead stirrer, the following are added: a mixed solvent (n-hexane/methyl chloride, 60/40 v/v), 2,6-di-t-butyl pyridine (0.007 M), 1,3,5-tri(2-methoxyisopropyl)benzene (0.044M), and isobutylene (2 M) at a temperature of −76° C. Polymerization is induced by the rapid addition of TiCl$_4$ (0.15 M) to the stirred charge. After 10 minutes of stirring the reaction is terminated by the addition of a 3 fold molar excess of allyltrimethylsilane (AllylSiMe$_3$) relative to the tert-chlorine end groups of the ø-(PIB—Cl)$_3$ that formed. After 60 minutes of further stirring at −76° C., the system is deactivated by introducing a few milliliters of aqueous NaHCO$_3$, and the (allyl-terminated polyisobutylene) product is isolated. The yield is 28 grams (85% of theoretical); M$_n$=3000 g/mol.

2. Preparation of ø-(PIB—CH$_2$—CH$_2$—CH$_2$—Br)$_3$: Anti-Markovnikov Addition of HBr to ø-(PIB-Allyl)$_3$:

A 100 mL three-neck flask is charged with heptane (50 mL) and allyl-telechelic polyisobutylene (10 grams), and air is bubbled through the solution for 30 minutes at 100° C. to activate the allylic end groups. Then the solution is cooled to approximately −10° C. and HBr gas is bubbled through the system for 10 minutes.

Dry HBr is generated by the reaction of aqueous (47%) hydrogen bromide and sulfuric acid (95 to 98%). After neutralizing the solution with aqueous NaHCO$_3$ (10%), the product is washed 3 times with water. Finally the solution is dried over magnesium sulfate for at least 12 hours (i.e., over night) and filtered. The solvent is then removed via a rotary evaporator. The product is a clear viscous liquid.

FIG. 1A shows the $^1$H NMR spectrum of the allyl-terminated PIB and the primary bromine-terminated PIB product (FIG. 1B). The formulae and the group assignments are indicated below for FIGS. 1A and 1B.

FIG. 1A

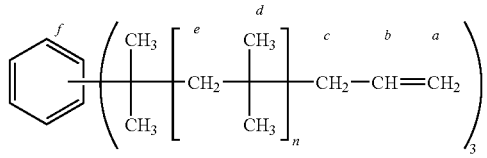

FIG. 1B

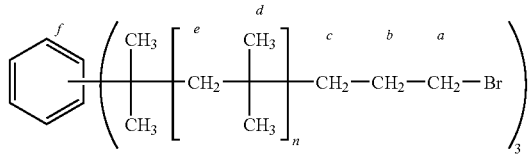

where n is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

It should be noted that the present invention is not limited to solely the use of allyl-terminated compounds, shown above, in the alcohol-terminated polyisobutylene production process disclosed herein. Instead, other straight or branched C$_3$ to C$_{12}$, C$_4$ to C$_{10}$, or even C$_5$ to C$_7$ alkenyl groups can be used so long as one double bond in such alkenyl groups is present at the end of the chain. Here, as well as elsewhere in the specification and claims, individual range limits can be combined to form alternative non-disclosed range limits.

As a further example regarding the above-mentioned alkenyl groups the following general formula is used to show the positioning of the end double bond:

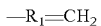

where R$_1$ is the remaining portion of the straight or branched alkenyl groups described above. In another embodiment, the alkenyl groups of the present invention contain only one double bond and this double bond is at the end of the chain as described above.

The olefinic (allylic) protons at 5 ppm present in spectrum (A) completely disappear upon anti-Markovnikov hydrobromination, as is shown in spectrum (B). The aromatic protons present in the 1,3,5-tri(2-methoxylsopropyl)benzene (initiator residue) provide an internal reference. Thus, integration of the terminal methylene protons of the —PIB—CH$_2$—CH$_2$—CH$_2$—Br relative to the three aromatic protons in the initiator fragment yields quantitative functionality information. The complete absence of allyl groups and/or secondary bromines indicates substantially 100% conversion to the target anti-Markovnikov product ø-(PIB—C$_2$—CH$_2$—CH$_2$—Br)$_3$.

3. Preparation of ø-(PIB—CH$_2$—CH$_2$—CH$_2$OH)$_3$ from ø-(PIB—CH$_2$—CH$_2$—CH$_2$—Br)$_3$:

The conversion of the terminal bromine product to a terminal primary hydroxyl group is performed by nucleophilic substitution on the bromine. A round bottom flask equipped with a stirrer is charged with a solution of ø-(PIB—CH$_2$—CH$_2$—CH$_2$—Br)$_3$ in THF. Then an aqueous solution of NaOH is added, and the charge is stirred for 2 hours at room temperature. Optionally, a phase transfer catalyst such as tetraethyl ammonium bromide can be added to speed up the reaction. The product is then washed 3 times with water, dried over magnesium sulfate overnight and filtered. Finally the solvent is removed via the use of a rotary evaporator. The product, a primary alcohol-terminated PIB product, is a clear viscous liquid.

In another embodiment, the present invention relates to a process for producing halogen-terminated PIBs (e.g. chlorine-terminated PIBs rather than the bromine containing compounds discussed above). These halogen-terminated PIBs can also be utilized in above process and converted to primary alcohol-terminated PIB compounds. Additionally, as is noted above, the present invention relates to the use of such PIB compounds in the production of polyurethanes, as well as a variety of other polymeric end products, such as methacrylates (via a reaction with methacryloyl chloride), hydrophobic adhesives (e.g., cyanoacrylate derivatives), epoxy resins, polyesters, etc.

In still another embodiment, the primary halogen-terminated PIB compounds of the present invention can be converted into PIB compounds that contain end epoxy groups, amine groups, etc. Previous efforts to inexpensively prepare primary halogen-terminated PIB compounds were fruitless and only resulted in compounds with tertiary terminal halogens.

As noted above, the primary alcohol-terminated PIBs are useful intermediates in the preparation of polyurethanes by reaction via conventional techniques, i.e., by the use of known isocyanates (e.g., 4,4'-methylenediphenyl diisocyanate, MDI) and chain extension agents (e.g., 1,4-butane diol, BDO). The great advantage of these polyurethanes (PUs) is their biostability imparted by the biostable PIB segment. Moreover, since PIB is known to be biocompatible, any PU made from the PIB compounds of the present invention is novel as well as biocompatible.

The primary terminal OH groups can be further derivatized to yield additional useful derivatives. For example, they can be converted to terminal cyanoacrylate groups which can be attached to living tissue and in this manner new tissue adhesives can be prepared.

In one embodiment of the present invention, the starting PIB segment can be mono-, di- tri, and multi-functional, and in this manner one can prepare di-terminal, tri-terminal, or other PIB derivatives. In another embodiment, the present invention makes it possible to prepare α,ω di-terminal (telechelic), tri-terminal, or other PIB derivatives. One of the most interesting PIB starting materials is arborescent-PIB (arb-PIB) that can carry many primary halogen termini, all of which can be converted to primary alcohol groups.

In another embodiment, the following equations describe further processes and compounds that can be produced via the present invention. As a general rule, all of the following reactions can be run at a 95% or better conversion rate.

(A) Cationic living isobutylene polymerization affords a first intermediate which is, for example, a tert-Cl— terminated PIB chain:

~~~C(CH$_3$)$_2$—[CH$_2$—C(CH$_3$)$_2$]$_n$—C$_2$—C(CH$_3$)$_2$—Cl     (A)

where ~~~ represents the remaining portion of a linear, star, hyperbranched, or arborescent molecule and n is defined as noted above. As would be apparent to those of skill in the art, ~~~ can in some instances represent another chlorine atom in order to permit the production of substantially linear di-terminal primary alcohol PIBs. Additionally, it should be noted that the present invention is not limited to the above specific linking groups (i.e., the —C(CH$_3$)$_2$) between the repeating PIB units and the remainder of the molecules of the present invention.

(B) The next step is the dehydrogenation of (A) to afford the second intermediate shown below:

~~~C(CH$_3$)$_2$—[CH$_2$—C(CH$_3$)$_2$]$_n$—CH$_2$—C(CH$_3$)=CH$_2$     (B).

(C) The third step is the anti-Markovnikov bromination of (B) to afford the primary bromide shown below:

~~~C(CH$_3$)$_2$—[CH$_2$—C(C$_3$)$_2$]$_n$—CH$_2$—CH(CH$_3$)—CH$_2$—Br     (C).

(D) The fourth step is the conversion of the primary bromide by the use of a base (e.g., NaOH, KOH, or tert-BuONa) to a primary hydroxyl group according to the following formula:

~~~C(CH$_3$)$_2$—[CH$_2$—C(CH$_3$)$_2$]$_n$—CH$_2$—CH(CH$_3$)—CH$_2$—OH     (D).

In another embodiment, the following reaction steps can be used to produce a primary alcohol-terminated PIB compound according to the present invention.

(B') Instead of the dehydrogenation, as outlined in (B), one can use an allyl silane such as trimethyl allyl silane to prepare an allyl terminated PIB:

~~~C(CH$_3$)$_2$—[CH$_2$—C(CH$_3$)$_2$]$_n$—CH$_2$—CH=CH$_2$     (B').

(C') Similarly to the reaction shown in (C) above, the (B') intermediate is converted to the primary bromide by an anti-Markovnikov reaction to yield the following compound:

~~~C(CH$_3$)$_2$—[CH$_2$—C(CH$_3$)$_2$]$_n$—CH$_2$—CH$_2$—CH$_2$—Br     (C').

(D') (C') can be converted to a primary alcohol-terminated compound as discussed above to yield the following compound:

~~~C(CH$_3$)$_2$—[CH$_2$—C(CH$_3$)$_2$]$_n$—CH$_2$—CH$_2$—CH$_2$—OH     (D').

As discussed above, in another embodiment the present invention relates to primary terminated polyisobutylene compounds having two or more primary termini selected from an amine groups or methacrylate groups. Again, as in other embodiments of the present invention, the following embodiments can be applied to linear, star, hyperbranched, or arborescent molecules with the number of repeating units in the PIB portion of such molecules being the same as defined as noted above.

4. Synthesis of Polyisobutylene Methacrylate Macromolecules (PIB—CH$_2$)$_3$-MA):

Synthesis of a primary methacrylate-terminated polyisobutylene is carried out according to the exemplary reaction scheme shown below:

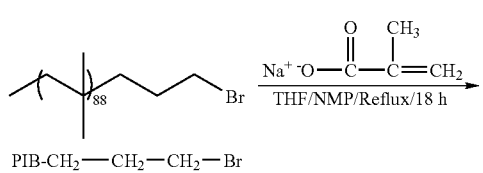

-continued

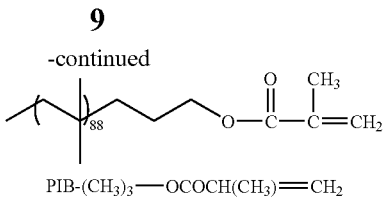

PIB-(CH₃)₃—OCOCH(CH₃)=CH₂

THF=20 mL=17.78 grams=59 wt %; NMP=10 mL=10.3 grams=34.24 wt %

To 1.0 grams of PIB—(CH$_2$)$_3$—Br ($M_n$=5160 grams/mole and $M_w/M_n$=1.065) dissolved in 20 mL of THF is added 10.0 mL NMP to increase the polarity of the medium. To this solution is added 1 gram of sodium methacrylate, and the mixture is refluxed at 80° C. for 18 hours. The charge is diluted by the addition of 50 mL hexanes and washed 3 times with excess water. The organic layer is separated, washed three times with distilled water and dried over MgSO$_4$. The hexanes are removed by a rotavap and the resulting polymer is dried under vacuum, and the yield of PIB—(CH$_2$)$_3$-MA is 0.95 grams (95%).

It should be noted that the above embodiment is not limited to just the use of sodium methacrylate, but rather other suitable methacrylate compounds could be used. Such compounds include, but are not limited to, alkaline methacrylate compounds.

Additionally, the present invention is not limited to solely the use of allyl-terminated compounds in the methacrylate-terminated polyisobutylene production process disclosed herein. Instead, other straight or branched C$_3$ to C$_{12}$, C$_4$ to C$_{10}$, or even C$_5$ to C$_7$ alkenyl groups can be used so long as one double bond in such alkenyl groups is present at the end of the chain. Here, as well as elsewhere in the specification and claims, individual range limits can be combined to form alternative non-disclosed range limits.

As a further example regarding the above-mentioned alkenyl groups the following general formula is used to show the positioning of the end double bond:

—R$_1$=CH$_2$ where R$_1$ is the remaining portion of the straight or branched alkenyl groups described above. In another embodiment, the alkenyl groups of the present invention contain only one double bond and this double bond is at the end of the chain as described above.

5. Synthesis of Amine-Terminated Polyisobutylene (PIB—(CH$_2$)$_3$—NH$_2$):

In this embodiment, the synthesis of PIB—(CH$_2$)$_3$—NH$_2$ involves two steps: (a) substitution of the terminal primary bromine to phthalimide-terminated polyisobutylene (PIB—(CH$_2$)$_3$-phthalimide); and (b) hydrazinolysis of the phthalimide terminated polyisobutylene to primary amine-terminated polyisobutylene (PIB—(CH$_2$)$_3$—NH$_2$).

(a) Synthesis of Phthalimide-Terminated Polyisobutylene (PIB—(CH$_2$)$_3$-Phthalimide):

Synthesis of a phthalimide-terminated polyisobutylene (PIB—(CH$_2$)$_3$-phthalimide) is carried out according to the reaction scheme shown below:

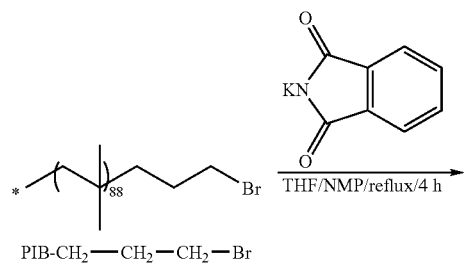

PIB-CH₂—CH₂—CH₂—Br

-continued

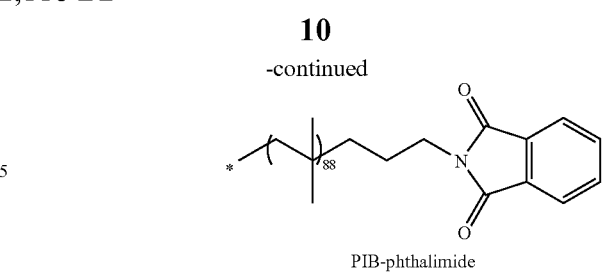

PIB-phthalimide

To 1.0 gram of PIB—(CH$_2$)$_3$—Br ($M_n$=5160 grams/mole and $M_w/M_n$=1.06) dissolved in 20 mL THF is added 10 mL of NMP to increase the polarity of the medium. To this solution is added 1.0 gram of potassium phthalimide and the mixture is refluxed at 80° C. for 4 hours. The reaction mixture is diluted by the addition of 50 mL hexanes and washed 3 times with excess water. The organic layer is separated, washed three times with distilled water and dried over MgSO$_4$. The hexanes are removed by a rotavap, and the resulting polymer is dried under vacuum. The yield of PIB—(CH$_2$)$_3$-phthalimide is 0.97 grams.

(b) Synthesis of Primary Amine-Terminated Polyisobutylene (PIB—(CH$_2$)$_3$—NH$_2$):

Synthesis of an amine-terminated polyisobutylene (PIB—(CH$_2$)$_3$—NH$_2$) is carried out according to the reaction scheme shown below:

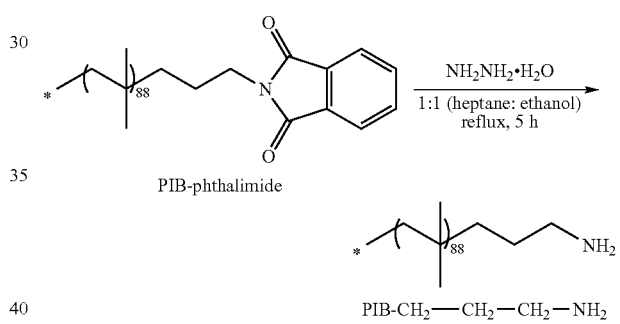

PIB-CH₂—CH₂—CH₂—NH₂

To 1.0 gram of PIB—(CH$_2$)$_3$-phthalimide dissolved in a mixture of 20 mL heptane and 20 mL of ethanol is added 3 grams of hydrazine hydrate. This mixture is then refluxed at 105° C. for 5 hours. Then the charge is diluted with 50 mL hexanes and washed 3 times with excess water. The organic layer is separated, washed three times with distilled water and dried over MgSO$_4$. The hexanes are removed by a rotavap and the polymer is dried under vacuum. The yield of PIB—(CH$_2$)$_3$—NH$_2$ is 0.96 grams.

It should be noted that the present invention is not limited to solely the use of allyl-terminated compounds, shown above, in the amine-terminated polyisobutylene production process disclosed herein. Instead other straight or branched C$_3$ to C$_{12}$, C$_4$ to C$_{10}$, or even C$_5$ to C$_7$ alkenyl groups can be used so long as one double bond in such alkenyl groups is present at the end of the chain. Here, as well as elsewhere in the specification and claims, individual range limits can be combined to form alternative non-disclosed range limits.

As a further example regarding the above-mentioned alkenyl groups the following general formula is used to show the positioning of the end double bond:

R$_1$=CH$_2$ where R$_1$ is the remaining portion of the straight or branched alkenyl groups described above. In another embodiment, the alkenyl groups of the present invention contain only one double bond and this double bond is at the end of the chain as described above.

In another embodiment, the present invention relates to a polyisobutylenes having at least two primary bromine termini as shown in the formula below:

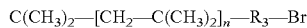
C(CH$_3$)$_2$—[CH$_2$—C(CH$_3$)$_2$]$_n$—R$_3$—Br where ~~~ represents the remaining portion of a linear, star, hyperbranched, or arborescent molecule and n is defined as noted above. As would be apparent to those of skill in the art, ~~~ can in some instances represent another bromine atom in order to permit the production of substantially linear di-terminal primary alcohol PIBs. In the above formula R$_3$ represents the remainder of the alkenyl group left after subjecting a suitable alkenyl-terminated compound to an anti-Markovnikov bromination step in accordance with the present invention. As would be apparent to those of skill in the art R$_3$ could be either a straight or branched C$_3$ to C$_{12}$, C$_4$ to C$_{10}$, or even C$_5$ to C$_7$ alkyl group (the result of the "starting" alkenyl group having only one double bond, with such double bond being present at the end of the chain as described above). In another embodiment, R$_3$ could be either a straight or branched C$_3$ to C$_{12}$, C$_4$ to C$_{10}$, or even C$_5$ to C$_7$ alkenyl group (the result of the "starting" alkenyl group having two or more double bonds, with one of the double bonds being present at the end of the chain as described above).

Telechelic Amine and Alcohol PIBs for Use in the Production of Various Polymer Compounds:

In another embodiment, the present invention relates to amine-telechelic polyisobutylenes (PIBs) that carry a certain amount of functional primary (—NH$_2$), secondary (—NH—R$_4$), or tertiary (═N—R$_4$) amine end groups where R$_4$ is as defined below. In yet another embodiment, the present invention relates to alcohol-telechelic PIBs that carry a certain amount of functional primary alcohol end groups (—OH).

The term telechelic (from the Greek telos=far, and chelos=claw) indicates that each and every terminus of a polymer molecule is fitted with a functional end group. In one embodiment of the present invention the functional end groups of the present invention are hydroxyl or amine end groups. In another embodiment of the present invention, each chain end of a hydroxyl- or an amine-telechelic PIB molecule carries about 1.0±0.05 functional groups (i.e., a total of about 2.0±0.05, i.e., better than about 95 mole percent).

As is noted above, in one embodiment the present invention relates to amine-telechelic polyisobutylenes (PIBs) are PIBs that carry primary (—NH$_2$), secondary (—NH—R$_4$), or tertiary (═N—R$_4$) amine end groups, where R$_4$ is selected from linear or branched C$_1$ to C$_{30}$ alkyl group, a linear or branched C$_2$ to C$_{30}$ alkenyl group, a linear or branched C$_2$ to C$_{30}$ alkynyl group. In another embodiment, R$_4$ is selected from linear or branched C$_1$ to C$_{20}$ alkyl group, a linear or branched C$_2$ to C$_{20}$ alkenyl group, a linear or branched C$_2$ to C$_{20}$ alkynyl group. In still another embodiment, R$_4$ is selected from linear or branched C$_1$ to C$_{10}$ alkyl group, a linear or branched C$_2$ to C$_{10}$ alkenyl group, a linear or branched C$_2$ to C$_{10}$ alkynyl group, or even C$_1$ to C$_5$ alkyl group, a linear or branched C$_2$ to C$_6$ alkenyl group, a linear or branched C$_2$ to C$_6$ alkynyl group. Here, as well as elsewhere in the specification and claims, individual range limits can be combined to form alternative non-disclosed range limits.

In yet another embodiment, R$_4$ is selected from either a methyl, ethyl, propyl, or butyl group, or even a methyl or ethyl group.

The simplest telechelic PIB molecule is the ditelechelic structure; for example, a PIB fitted with one —NH$_2$ group at either end of the molecule: H$_2$N—PIB—NH$_2$. A PIB carrying only one —NH$_2$ terminus (i.e., PIB—NH$_2$) is not an amine-telechelic PIB within the definition known to those of skill in the art. A three-arm star amine-telechelic PIB (i.e., a tri-telechelic PIB) carries three —NH$_2$ groups, one —NH$_2$ group at each arm end: abbreviated R$_5$(PIB—NH$_2$)$_3$, where the R$_5$ is selected from any tri-substituted aromatic group. In another embodiment, in the case of a three-arm star amine-telechelic PIB, R$_5$ can be any suitable functional group that can be tri-substituted with three PIB—NH$_2$ groups. A hyperbranched or arborescent amine-telechelic PIB carries many —NH$_2$ termini, because all the branch ends carry an —NH$_2$ terminus (multi-telechelic PIB). In another embodiment, the primary NH$_2$ groups mentioned above can be replaced by the afore-mentioned secondary (—NH—R$_4$), or tertiary (═N—R$_4$) amine end groups with R$_4$ being defined above.

Molecules with less than about 1.0±0.05 hydroxyl or amine groups per chain end, and synthesis methods that yield less than about 1.0±0.05 hydroxyl or amine groups per chain end are of little or no practical interest in the production of compounds for use in the production of polyurethanes and/or polyureas. This stringent requirement must be met because these telechelic PIBs are designed to be used as intermediates for the production of polyurethanes and polyureas, and precise starting material stoichiometry is required for the preparation of polyurethane and/or polyurea compounds having optimum mechanical properties. In the absence of precise (i.e., about 1.0±0.05) terminal functionality, the preparation of high quality polyurethanes and polyureas is not possible.

Polymers obtained by the reaction of hydroxy-ditelechelic PIB (i.e., HO—PIB—OH) and diisocyanates (e.g., MDI) contain urethane (carbamate) linkages:

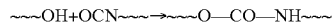
~~~OH+OCN~~~→~~~O—CO—NH~~~ and are called polyurethanes, where in this case ~~~ represents the remainder of the polyurethane molecule. Similarly, polymers prepared by amine-ditelechelic PIB (H$_2$N—PIB—NH$_2$) plus diisocyanates contain urea linkages:

~~~NH$_2$+OCN~~~→~~~NH—CO—NH~~~ and are called polyureas, where in this case ~~~ represents the remainder of the polyurea molecule.

Finally, the overall cost of the products, as determined by the cost of the starting materials and the procedures, is of decisive importance because only low cost commercially feasible simple syntheses are considered.

Although the present invention specifically discloses a method for producing various alcohol-telechelic PIBs and amine-telechelic PIBs terminated with at least two alcohol or amine groups, the present invention is not limited thereto. Rather, the present invention can be used to produce a wide variety of PIB molecular geometries, where such molecules are terminated with two or more primary alcohols or two or more amine groups be they primary amine groups, secondary amine groups, or tertiary amine groups.

In one embodiment, the primary alcohols that can be used as terminating groups in the present invention include, but are not limited to, any straight or branched chain primary alcohol substituent group having from 1 to about 12 carbon atoms, or from 1 to about 10 carbon atoms, or from 1 to about 8, or from about 1 to about 6 carbon atoms, or even from about 2 to about 5 carbon atoms. Here, as well as elsewhere in the specification and claims, individual range limits can be combined to form alternative non-disclosed range limits.

In another embodiment, the present invention relates to linear, or star-shaped, or hyperbranched, or arborescent PIB compounds, where such compounds contain two or more primary alcohol-terminated segments, amine-terminated segments, or amine-containing segments. Such molecular geometries are known in the art, and a discussion herein is omitted for the sake of brevity. In another embodiment, the present invention relates to star-shaped molecules that contain a center cyclic group (e.g., an aromatic group) to which three or more primary alcohol-terminated PIB arms are attached, or three or more amine-containing PIB arms are attached.

The following examples are exemplary in nature and the present invention is not limited thereto. Rather, as is noted above, the present invention relates to the production and/or manufacture of various primary alcohol-terminated PIB compounds and polyurethane compounds made therefrom.

EXAMPLES

The following example concerns the synthesis of a primary hydroxyl-terminated polyisobutylene in three steps as is discussed above:

1. Preparation of a Star Molecule with Three Allyl-Terminated PIB Arms (ø-(PIB-Allyl)₃):

The synthesis of ø-(PIB-Allyl)₃ followed the procedure described by Lech Wilczek and Joseph P. Kennedy in *The Journal of Polymer Science: Part A: Polymer Chemistry*, 25, pp. 3255 through 3265 (1987), the disclosure of which is incorporated by reference herein in its entirety.

The first step involves the polymerization of isobutylene to tert-chlorine-terminated PIB by the 1,3,5-tri(2-methoxyisopropyl)benzene/TiCl₄ system under a blanket of N₂ in a drybox. Next, in a 500 mL three-neck round bottom glass flask, equipped with an overhead stirrer, the following are added: a mixed solvent (n-hexane/methyl chloride, 60/40 v/v), 2,6-di-t-butyl pyridine (0.007 M), 1,3,5-tri(2-methoxyisopropyl)benzene (0.044M), and isobutylene (2 M) at a temperature of −76° C. Polymerization is induced by the rapid addition of TiCl₄ (0.15 M) to the stirred charge. After 10 minutes of stirring the reaction is terminated by the addition of a 3 fold molar excess of allyltrimethylsilane (AllylSiMe₃) relative to the tert-chlorine end groups of the ø-(PIB—Cl)₃ that formed. After 60 minutes of further stirring at −76° C., the system is deactivated by introducing a few milliliters of aqueous NaHCO₃, and the (allyl-terminated polyisobutylene) product is isolated. The yield is 28 grams (85% of theoretical); M$_n$=3000 g/mol.

2. Preparation of ø-(PIB—CH₂—CH₂—CH₂—Br)₃: Anti-Markovnikov Addition of HBr to ø-(PIB-Allyl)₃:

A 100 mL three-neck flask is charged with heptane (50 mL) and allyl-telechelic polyisobutylene (10 grams), and air is bubbled through the solution for 30 minutes at 100° C. to activate the allylic end groups. Then the solution is cooled to approximately −10° C. and HBr gas is bubbled through the system for 10 minutes.

Dry HBr is generated by the reaction of aqueous (47%) hydrogen bromide and sulfuric acid (95 to 98%). After neutralizing the solution with aqueous NaHCO₃ (10%), the product is washed 3 times with water. Finally the solution is dried over magnesium sulfate for at least 12 hours (i.e., over night) and filtered. The solvent is then removed via a rotary evaporator. The product is a clear viscous liquid.

FIG. 1A shows the ¹H NMR spectrum of the allyl-terminated PIB and the primary bromine-terminated PIB product (FIG. 1B). The formulae and the group assignments are indicated below for FIGS. 1A and 1B.

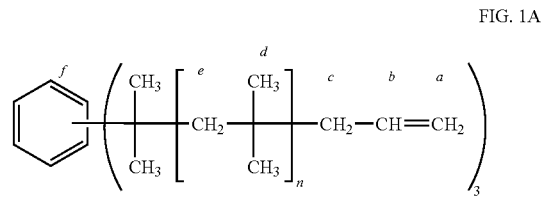

FIG. 1A

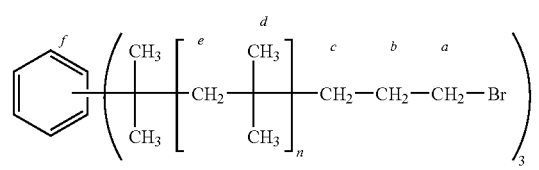

FIG. 1B where n is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

It should be noted that the present invention is not limited to solely the use of allyl-terminated compounds, shown above, in the alcohol-terminated polyisobutylene production process disclosed herein. Instead, other straight or branched C₃ to C₁₂, C₄ to C₁₀, or even C₅ to C₇ alkenyl groups can be used so long as one double bond in such alkenyl groups is present at the end of the chain. Here, as well as elsewhere in the specification and claims, individual range limits can be combined to form alternative non-disclosed range limits.

As a further example regarding the above-mentioned alkenyl groups the following general formula is used to show the positioning of the end double bond:

—R₁=CH₂ where R₁ is the remaining portion of the straight or branched alkenyl groups described above. In another embodiment, the alkenyl groups of the present invention contain only one double bond and this double bond is at the end of the chain as described above.

The olefinic (allylic) protons at 5 ppm present in spectrum (A) completely disappear upon anti-Markovnikov hydrobromination, as is shown in spectrum (B). The aromatic protons present in the 1,3,5-tri(2-methoxyisopropyl)benzene (initiator residue) provide an internal reference. Thus, integration of the terminal methylene protons of the —PIB—CH₂—CH₂—CH₂—Br relative to the three aromatic protons in the initiator fragment yields quantitative functionality information. The complete absence of allyl groups and/or secondary bromines indicates substantially 100% conversion to the target anti-Markovnikov product ø-(PIB—CH₂—CH₂—CH₂—Br)₃:

3. Preparation of ø-(PIB—CH₂—CH₂—CH₂—OH)₃ from ø-(PIB—CH₂—CH₂—CH₂—Br)₃:

The conversion of the terminal bromine product to a terminal primary hydroxyl group is performed by nucleophilic substitution on the bromine. A round bottom flask equipped with a stirrer is charged with a solution of ø-(PIB—CH₂—CH₂—CH₂—Br)₃ in THF. Then an aqueous solution of NaOH is added, and the charge is stirred for 2 hours at room temperature. Optionally, a phase transfer catalyst such as tetraethyl ammonium bromide can be added to speed up the reaction. The product is then washed 3 times with water, dried over magnesium sulfate overnight and filtered. Finally the solvent is removed via the use of a rotary evaporator. The product, a primary alcohol-terminated PIB product, is a clear viscous liquid.

In another embodiment, the present invention relates to a process for producing halogen-terminated PIBs (e.g., chlorine-terminated PIBs rather than the bromine containing compounds discussed above). These halogen-terminated PIBs can also be utilized in above process and converted to primary alcohol-terminated PIB compounds. Additionally, as is noted above, the present invention relates to the use of such PIB compounds in the production of polyurethanes, as well as a variety of other polymeric end products, such as methacrylates (via a reaction with methacryloyl chloride), hydrophobic adhesives (e.g., cyanoacrylate derivatives), epoxy resins, polyesters, etc.

In still another embodiment, the primary halogen-terminated PIB compounds of the present invention can be converted into PIB compounds that contain end epoxy groups, amine groups, etc. Previous efforts to inexpensively prepare primary halogen-terminated PIB compounds were fruitless and only resulted in compounds with tertiary terminal halogens.

As noted above, the primary alcohol-terminated PIBs are useful intermediates in the preparation of polyurethanes by reaction via conventional techniques, i.e., by the use of known isocyanates (e.g., 4,4'-methylenediphenyl diisocyanate, MDI) and chain extension agents (e.g., 1,4-butane dial, BDO). The great advantage of these polyurethanes (PUs) is their biostability imparted by the biostable PIB segment. Moreover, since PIB is known to be biocompatible, any PU made from the PIB compounds of the present invention is novel as well as biocompatible.

The primary terminal OH groups can be further derivatized to yield additional useful derivatives. For example, they can be converted to terminal cyanoacrylate groups which can be attached to living tissue and in this manner new tissue adhesives can be prepared.

In one embodiment of the present invention, the starting PIB segment can be mono-, di- tri, and multi-functional, and in this manner one can prepare di-terminal, tri-terminal, or other PIB derivatives. In another embodiment, the present invention makes it possible to prepare α,ω di-terminal (telechelic), tri-terminal, or other PIB derivatives. One of the most interesting PIB starting materials is arborescent-PIB (arb-PIB) that can carry many primary halogen termini, all of which can be converted to primary alcohol groups.

In another embodiment, the following equations describe further processes and compounds that can be produced via the present invention. As a general rule, all of the following reactions can be run at a 95% or better conversion rate.

(A) Cationic living isobutylene polymerization affords a first intermediate which is, for example, a tert-Cl— terminated PIB chain:

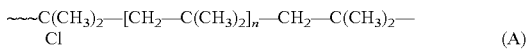  (A)

where ~~~ represents the remaining portion of a linear, star, hyperbranched, or arborescent molecule and n is defined as noted above. As would be apparent to those of skill in the art, ~~~ can in some instances represent another chlorine atom in order to permit the production of substantially linear di-terminal primary alcohol PIBs. Additionally, it should be noted that the present invention is not limited to the above specific linking groups (i.e., the —C(CH$_3$)$_2$) between the repeating PIB units and the remainder of the molecules of the present invention.

(B) The next step is the dehydrogenation of (A) to afford the second intermediate shown below:

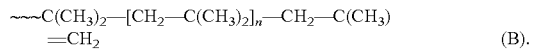  (B).

(C) The third step is the anti-Markovnikov bromination of (B) to afford the primary bromide shown below:

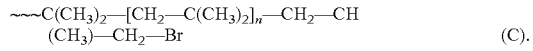  (C).

(D) The fourth step is the conversion of the primary bromide by the use of a base (e.g., NaOH, KOH, or tert-BuONa) to a primary hydroxyl group according to the following formula:

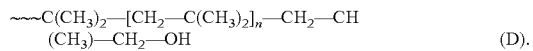  (D).

In another embodiment, the following reaction steps can be used to produce a primary alcohol-terminated PIB compound according to the present invention.

(B') Instead of the dehydrogenation, as outlined in (B), one can use an allyl silane such as trimethyl allyl silane to prepare an allyl terminated PIB:

  (B').

(C') Similarly to the reaction shown in (C) above, the (B') intermediate is converted to the primary bromide by an anti-Markovnikov reaction to yield the following compound:

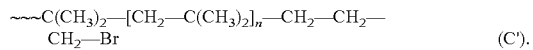  (C').

(D') (C') can be converted to a primary alcohol-terminated compound as discussed above to yield the following compound:

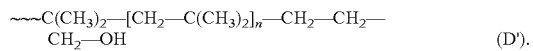  (D').

4. The structure, synthesis and characterization of H$_2$N—PIB—NH$_2$

The detailed structure of this example, the amine-ditelechelic PIB, is defined by the following Formula. However, the present invention is not limited thereto.

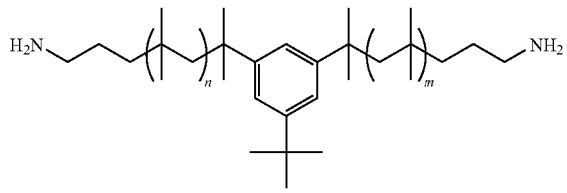

where n and m are each independently selected from an integer in the range of from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

The above compound can be produced from a corresponding brominated structure as shown above in (C). The following chemical equations summarize the synthesis method for the above compound:

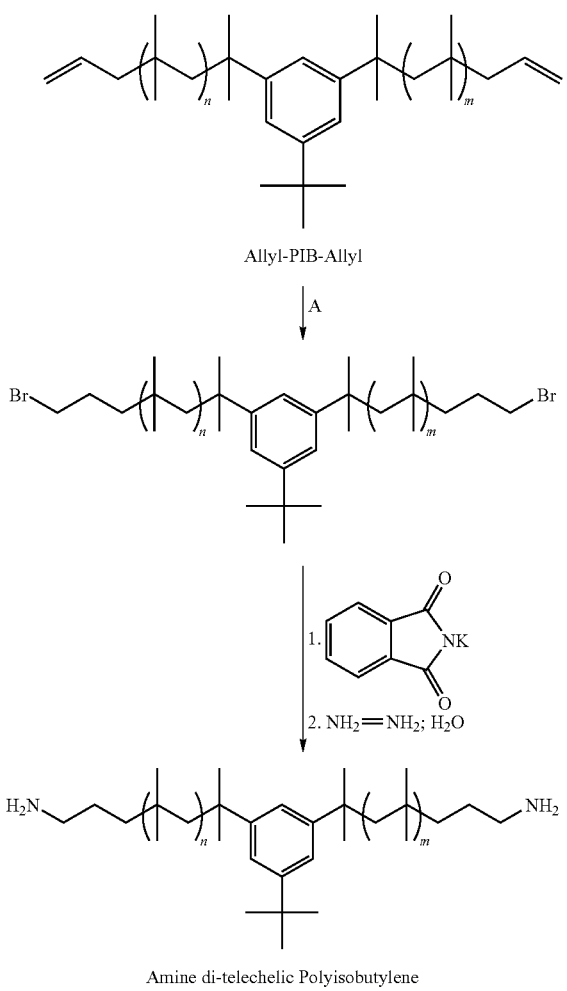

Amine di-telechelic Polyisobutylene where n and m are each independently selected from an integer in the range of from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

Additionally, the reaction conditions at A are: 30 grams of polymer, 150 mL of heptane (103 grams), reflux at 110° C. for 30 minutes, followed by passing HBr over the polymer solutions for 5 minutes at 0° C.

The Allyl-PIB-Allyl is then converted to the telechelic primary bromide, Br—(CH$_2$)$_3$—PIB—(CH$_2$)$_3$—Br, as described in above. Next, the Br—(CH$_2$)$_3$—PIB—(CH$_2$)$_3$—Br is converted by using: (1) potassium phthalimide; and (2) hydrazine hydrate to yield the target ditelechelic amine: NH$_2$—(CH$_2$)$_3$—PIB—(CH$_2$)$_3$—NH$_2$.

Figure 2:
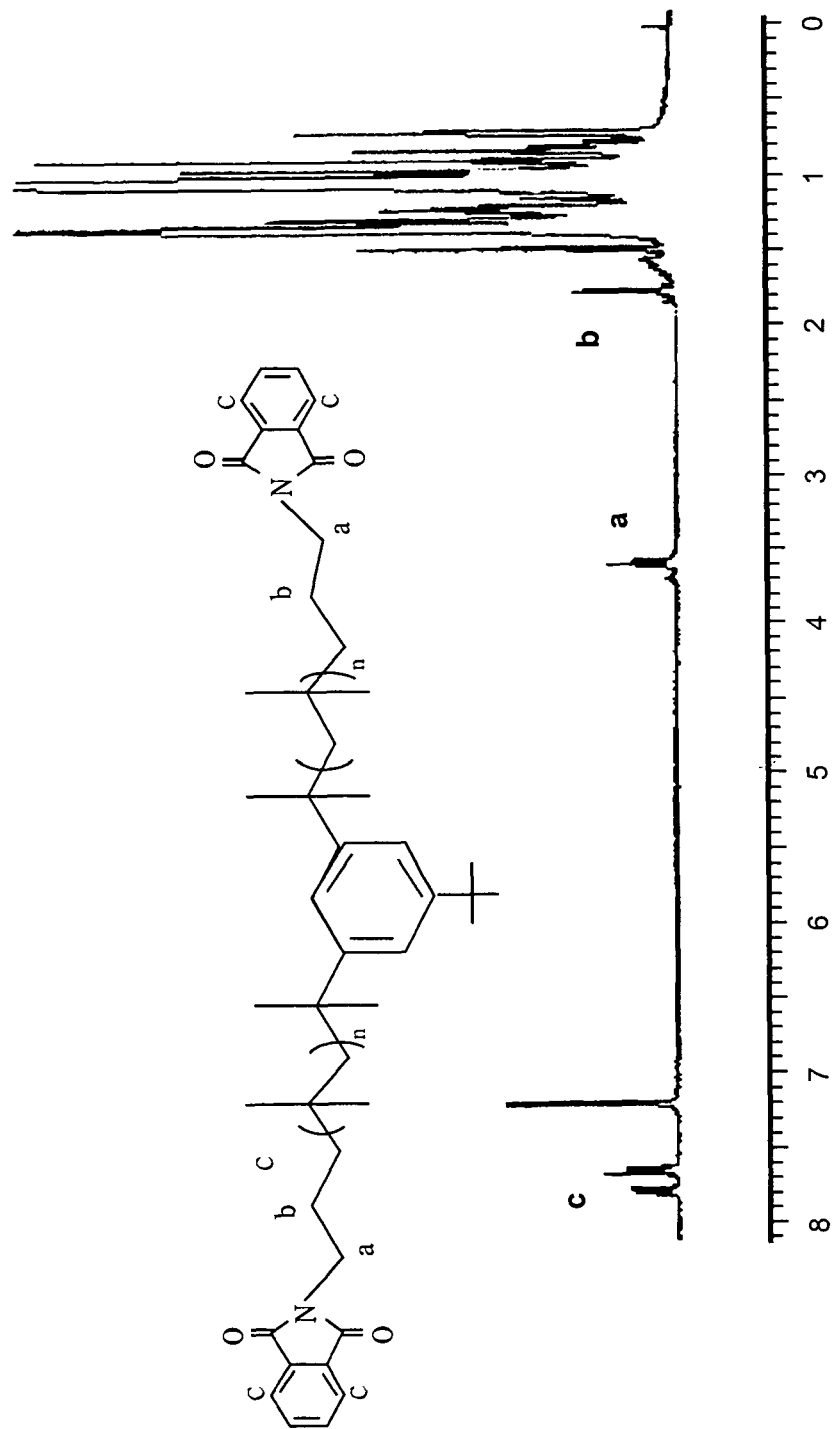
FIG. 2 is a $^1$H NMR spectrum of phthalimide-telechelic polyisobutylene.

Following the above process, 16 grams of bromo-ditelechelic polyisobutylene (0.003 mol) is dissolved in 320 mL dry THF. Then, 160 mL of NMP and phthalimide potassium (2.2 grams, 0.012 moles) are added to this solution. Next, the solution is heated to reflux at 80° C. for 8 hours. The product is then dissolved in 100 mL of hexanes, extracted 3 times with water and dried over magnesium sulfate. The structure of the intermediate is ascertained by $^1$H NMR spectroscopy. FIG. 2, below, shows the $^1$H NMR spectrum of phthalimide-telechelic polyisobutylene together with assignments.

Figure 3:
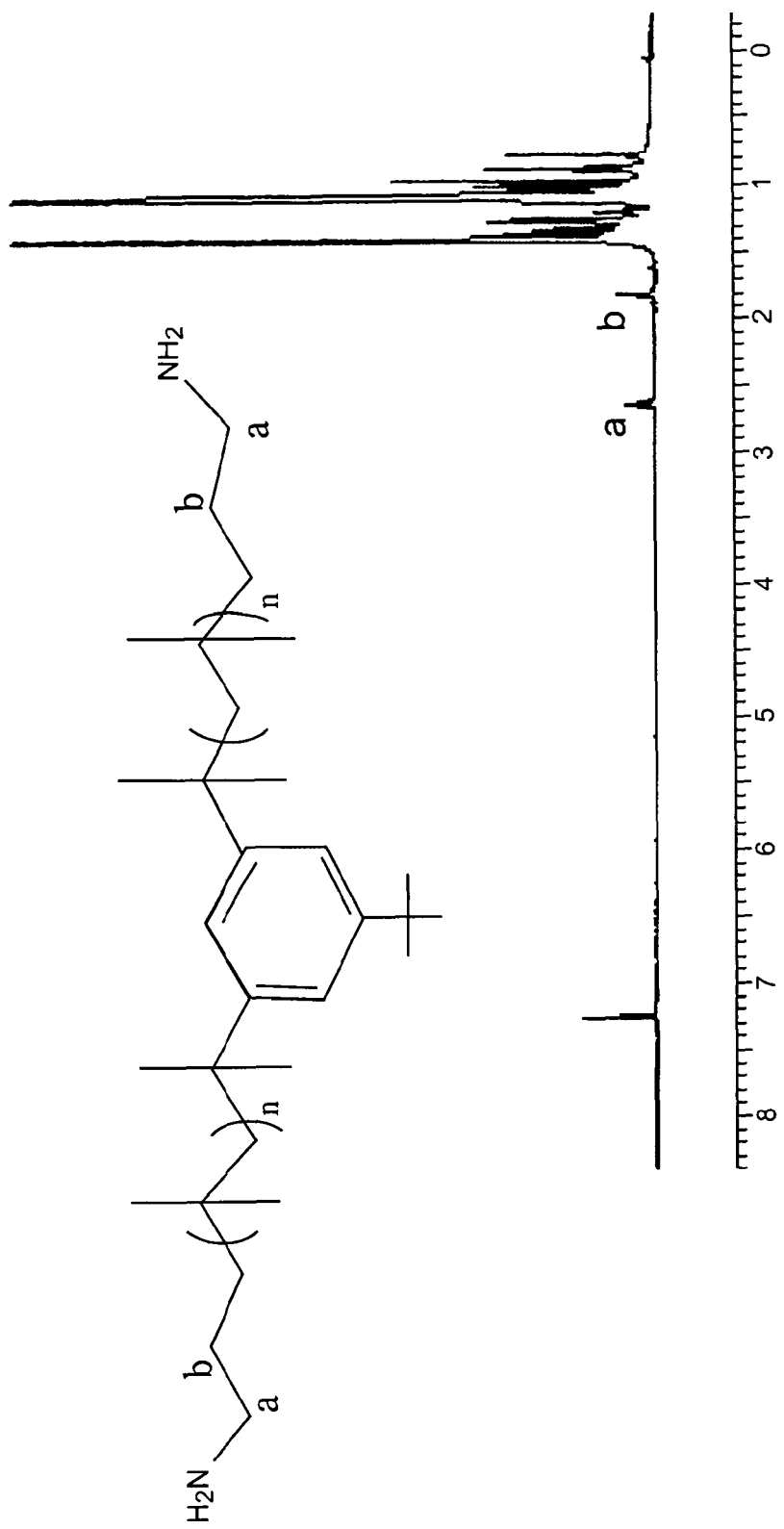
FIG. 3 is a $^1$H NMR spectrum of amine-telechelic polyisobutylene.

Then, the phthalimide-telechelic polyisobutylene (14 grams, 0.0025 moles) is dissolved in 280 mL of heptane, then 280 mL of ethanol and hydrazine hydrate (3.2 grams, 0.1 moles) are added thereto, and the solution is heated to reflux at 110° C. for 6 hours. The product is dissolved in hexanes, extracted 3 times with water, dried over magnesium sulfate, and the hexanes are removed by a rotavap. The structure of the target product is ascertained by $^1$H NMR spectroscopy. FIG. 3 shows the $^1$H NMR spectrum of amine-telechelic polyisobutylene together with assignments.

5. The Synthesis and Characterization of PIB-Based Polyurethanes and Polyureas:

(a). Polyurethanes:

(1) The Synthesis of the HO—PIB—OH Starting Material:

The synthesis of HO—PIB—OH is as described above. Thus, the starting material, a commercially available (Kaneka Inc.) allyl-ditelechelic PIB ($M_w$=5,500 g/mol) is hydro-brominated by dissolving it in heptane and bubbling HBr through the solution for 30 minutes at 70° C. Then the product is dissolved in THF, aqueous KOH and n-methylpyrrolidone are added, and the system is re-fluxed for 24 hours at 100° C. The structure of the HO—PIB—OH is ascertained by proton NMR spectroscopy.

(2) The Synthesis of a PIB-Based Polyurethane and Demonstration of its Oxidative Stability:

The polyurethane is obtained by reaction of the HO—PIB—OH with methylene-bis-phenyl isocyanate (MDI). The following equations describe the synthesis strategy used:

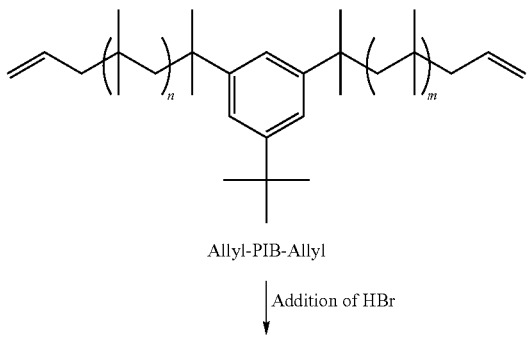

Allyl-PIB-Allyl

↓ Addition of HBr

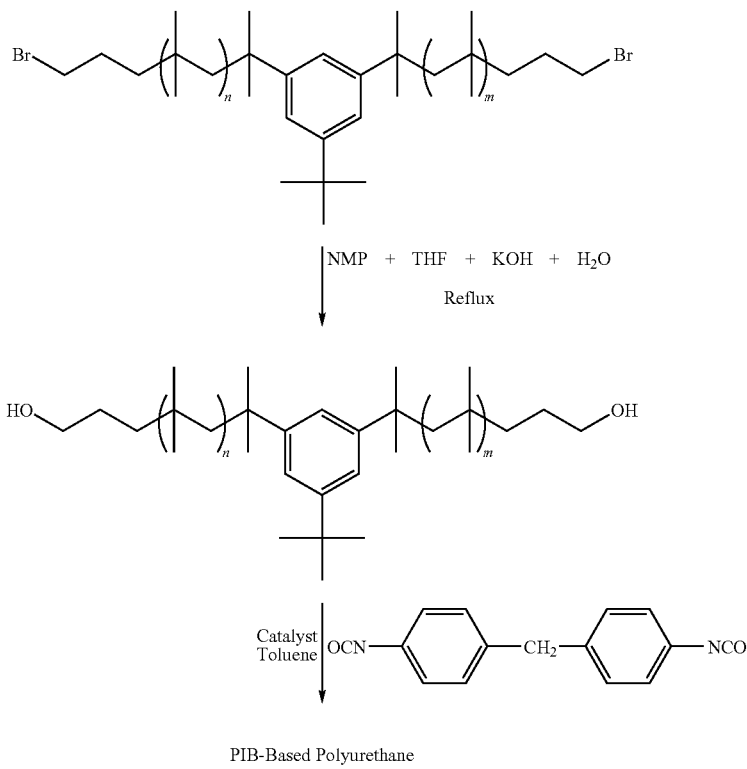

PIB-Based Polyurethane where n and m are each independently selected from an integer in the range of from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

Thus, HO—PIB—OH (2.2 grams, $M_n$=5,500 g/mol, hydroxyl equivalent 0.0008 mole) is dissolved in dry toluene (12 mL) and freshly distilled MEN (0.3 grams, 0.0012 moles of isocyanate) and tin dioctoate (0.03 mL) catalyst are added under a dry nitrogen atmosphere. The charge is then heated for 8 hours at 70° C., cooled to room temperature, and poured in a rectangular (5 cm×5 cm) Teflon mold. The system is air dried overnight and finally dried in a drying oven at 70° C. for 24 hours. The polyurethane product is a pale yellow supple rubbery sheet, soluble in THF. Manual examination reveals good mechanical properties.

The oxidative resistance of the polyurethane is tested by placing small amounts (approximately 0.5 grams) of pre-weighed samples in concentrated (65%) nitric acid in a 25 mL glass vial, and gently agitating the system at room temperature. Concentrated nitric acid is recognized to be one of the most aggressive and corrosive oxidizing agents. After 24 and 48 hours the appearance of the samples is examined visually and their weight loss determined gravimetrically by using the following expression:

$$W_{loss}=(W_b-W_a/W_b)100$$

where $W_{loss}$ is percent weight loss and $W_b$ and $W_a$ are the weights of the samples before and after nitric acid exposure, respectively. The weight loss is experimentally determined by removing the pre-weighed samples from the nitric acid, rinsing them thoroughly with water, drying them till weight constancy (approximately 24 hours), and weighed again. For comparison, the same procedure is also carried out with a "control" polyurethane prepared using a HO—PDMS—OH and MDI, and with another commercially available polyurethane (AorTech Biomaterials, Batch # 60802, E2A pellets sample).

The control polyurethane is prepared as follows: 1 gram (0.0002 moles) of hydroxy-ditelechelic polydimethylsiloxane (DMS-C21, Gelest, $M_n$=4500-5500 g/mol) is dissolved in 10 mL of toluene, and freshly distilled MDI (0.11 grams, 0.0002 moles) followed by (0.03 mL) tin octoate catalyst are added under a dry nitrogen atmosphere. The charge is heated for 8 hours at 70° C., cooled to room temperature, and poured in a rectangular (5 cm×5 cm) Teflon mold. The polyurethane sheet that is produced is air dried overnight and finally dried in a drying oven at 70° C. for 24 hours. The product is a pale yellow supple rubbery sheet, soluble in THF. Manual examination reveals good mechanical properties.

Table 1 summarizes the results of aggressive oxidative degradation test performed with PIB-, PDMS-based polyurethanes and a PIB-based polyurea. The oxidant is 65% $HNO_3$ at room temperature.

TABLE 1

| Materials | Time of exposure to concentrated HNO₃ | Weight Loss in Percent | Observations |
|---|---|---|---|
| PIB-Based (HO-PIB-OH) Polyurethane | 1 hour | 0 | No visible change |
| | 4 hours | 0 | No visible change |
| | 24 hours | 0 | No visible change |
| | 48 hours | 0 | Deep brown discoloration, sample becomes weak |
| PDMS-based (HO-PDMS-OH) Control Polyurethane | 30 minutes | 40 | Sample disintegrates to pasty mass adhering to glass |
| | 2 hours | 60 | Sample largely dissolved, some discolored jelly mass remains |
| | 4 hours | 90 | Sample largely dissolved, some discolored jelly mass remains |
| Commercial Polyurethane (AorTech) | 30 minutes | 50 | Sample disintegrated, some discolored jelly mass remains |
| | 1.5 hours | 70 | Sample disintegrated, some discolored jelly mass remains |
| | 4 hours | 95 | Sample disintegrated, some discolored jelly mass remains |
| PIB-Based (H₂N-PIB-NH₂) Polyurea | 1 hours | 0 | No visible change |
| | 4 hours | 0 | No visible change |
| | 24 hours | 0 | No visible change |
| | 48 hours | 0 | Deep brown discoloration, sample becomes weak |

According to the data, the PIB-based polyurethanes and polyureas (prepared with HO—PIB—OH/MDI and H$_2$N—PIB—NH$_2$/MDI) do not degrade after 24 hours when exposed to concentrated HNO$_3$ at room temperature. Oxidative resistance is demonstrated by the negligible weight loss of the polyurethane and polyurea films. After 48 hours exposure to concentrated HNO$_3$ both the PIB-based polyurethane and polyurea films exhibit deep brown discoloration and a visible weakening of the samples. In contrast, the control polyurethane prepared with HO—PDMS—OH/MDI, and a commercial polyurethane (i.e., a material considered highly oxidatively stable) completely degrades, and becomes largely soluble in the acid after less than 4 hours of exposure.

While not wishing to be bound to any one theory, the spectacular oxidative resistance of the PIB-based polyurethane and polyurethane formed in accordance with the synthesis processes of the present invention is most likely due to the protection of the vulnerable urethane (carbamate) and urea bonds by the inert PIB chains/domains. In contrast, the PDMS chains/domains cannot impart protection against the attack of the strong oxidizing acid.

(b) Polyureas:

(1) The Synthesis of PIB-Based Polyureas and Demonstration of their Oxidative Stability:

To H$_2$N—PIB—NH$_2$ (1.5 grams, M$_n$=5,500 g/mol, amine equivalent 0.00054 moles) dissolved in dry toluene (10 mL) is added freshly distilled MDI (0.125 grams, 0.0005 moles), with stirring, under a dry nitrogen atmosphere. Within a minute the solution becomes viscous. It is then diluted with 5 mL of toluene and poured in a rectangular (5 cm×5 cm) Teflon mold. The system is air dried overnight and finally dried in a drying oven at 70° C. for 24 hours. The polyurea product is a pale yellow supple rubbery sheet, soluble in THF. Manual examination reveals reasonable mechanical properties.

The oxidative stability of the polyurea is tested by exposing the sample to concentrated HNO$_3$ at room temperature (see Table 1 above). The last entry in Table 1 shows data relating to this Example. Evidently, the PIB-based polyurea resists oxidation under the harsh conditions detailed above for 24 hours.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method for producing a primary alcohol-terminated polyisobutylene compound comprising the steps of:
   (A) providing an allyl-terminated polyisobutylene having at least two allyl termini, wherein the allyl termini are formed by the addition of straight C$_3$ to C$_{12}$ allyl groups having a double bond present at the end of the allyl group;
   (B) subjecting the allyl-terminated polyisobutylene to anti-Markovnikov bromination to form a primary bromine-terminated polyisobutylene compound having at least two primary bromine termini;
   (C) converting the primary bromine-terminated polyisobutylene compound to a primary alcohol-terminated polyisobutylene via a base reaction, the primary alcohol-terminated polyisobutylene having at least two primary alcohol termini; and
   (D) recovering the primary alcohol-terminated polyisobutylene.

2. The method of claim 1, wherein the allyl termini are —CH$_2$—CH=CH$_2$.

3. The method of claim 1, wherein the anti-Markovnikov bromination reaction of Step (B) utilizes HBr.

4. The method of claim 1, wherein the primary alcohol-terminated polyisobutylene compound is a linear molecule.

5. The method of claim 1, wherein the primary alcohol-terminated polyisobutylene compound is a star molecule.

6. The method of claim 1, wherein the primary alcohol-terminated polyisobutylene compound is a hyperbranched molecule.

7. The method of claim 1, wherein the primary alcohol-terminated polyisobutylene compound is an arborescent molecule.

* * * * *